US005674502A

United States Patent [19]

Ennis

[11] Patent Number: 5,674,502
[45] Date of Patent: Oct. 7, 1997

[54] CROSS-REACTIVE INFLUENZA A IMMUNIZATION

[75] Inventor: Francis A. Ennis, Shrewsbury, Mass.

[73] Assignee: University of Massachusetts Medical Center, Worcester, Mass.

[21] Appl. No.: 462,963

[22] Filed: Jun. 5, 1995

Related U.S. Application Data

[63] Continuation of Ser. No. 419,513, Apr. 7, 1995, which is a continuation of Ser. No. 42,884, Apr. 5, 1993, abandoned, which is a continuation-in-part of Ser. No. 564,714, Aug. 8, 1990, abandoned.

[51] Int. Cl.$^{6}$ ..................... A61K 39/12; A61K 39/145; A61K 39/00; A61K 39/38

[52] U.S. Cl. ..................... 424/206.1; 424/184.1; 424/204.1; 424/205.1

[58] Field of Search ..................... 424/278.1, 184.1, 424/204.1, 206.1

[56] References Cited

U.S. PATENT DOCUMENTS 4,803,072 2/1989 Dalton et al. ..................... 424/85.5

FOREIGN PATENT DOCUMENTS 0 176 493 A1 8/1985 European Pat. Off. .
0 366 238 A2 8/1989 European Pat. Off. .
WO 88/01875 9/1987 WIPO .
WO 92/02250 2/1992 WIPO .
WO 93/15763 8/1993 WIPO .

OTHER PUBLICATIONS

Wraith, David C. et al., "Purified Influenza Virus Nucleoprotein Protects Mice from Lethal Infection," *J. Gen. Virol.* 68:433–440 (1987).

Bennink, Jack R. et al., "Anti-Influenza Virus Cytotoxic T Lymphocytes Recognize the Three Viral Polymerases and a Nonstructural Protein: Responsiveness to Individual Viral Antigens Is Major Histocompatibility Complex Controlled," *J. Gen. Virol.* 61(4):1098–1102 (1987).

Yamada, Akio et al., "Influenza Virus Hemagglutinin-Specific Cytotoxic T Cell Response Induced by Polypeptide Produced in *Escherichia coli*," *J. Exp. Med.* 162:663–674 (1985).

Kuwano, Koichi et al., "Active Immunization Against Virus Infections Due to Antigenic Drift by Induction of Crtossreactive Cytotoxic T Lymphocytes," *J. Exp. Med.* 169:1361–1371 (1989).

Kuwano, Koichi et al., "Ha2 Subunit of Influenza A H1 and H2 Subtype Viruses Induces a Protective Cross-Reactive Cytotoxic T Lymphocyte Resonse," *J. Immunol.* 140:1264–1268 (1988).

Kuwano, Koichi and Ennis, Francis, "Cross-reactive protection against influenza A virus infections by an NS2-specific CTL clone," Chemical Abstracts 113: Abstract No.: 130459C, p. 499 (1990).

Kingsman, Genetic Engineering, Chapter 12, Blackwell Scientific Publications (Oxford, GB), 1988.

Young et al., "Efficient Expression of Influenza Virus NS1," *PNAS* 80:6105–6109 (1983).

Smith, Geoffrey L. et al., "Synthesis and Cellular Location of Ten Influenza Polypeptides Individually Expressed by Recombinant Vaccinia Viruses," *Virology* 160(2):336–345 (1987).

Shaw, Michael W. et al., "Immunologic Studies on the Influenza A Virus Nonstructural Protein $NS_1$," *J. Exp. Med.* 156:243–254 (1982).

Kuwano, Koichi et al., "Cross-Reactive Protection Against Influenza A Virus Infections," *Virology,* 178:174–179 (1990).

Cossins, Judy et al., "Precise Prediction of a $K^k$-Restricted Cytotoxic T Cell Epitope in the NS1 Protein of Influenza Virus Using an MHC Allele-Specific Motif," *Virology,* 19 (31):289–295 (1993).

Hackett, Charles J. et al., "Influenza virus infection elicits class II major histocompatiility complex-restricted T cells specific for an epitope identified in the NS1 non-structural protein," *J. of General Virology,* 73:1339–1343 (1992).

*Primary Examiner*—Lynette F. Smith
*Attorney, Agent, or Firm*—Hamilton, Brook, Smith & Reynolds, P.C.

[57] ABSTRACT

This disclosure relates to methods and compositions for stimulating in an individual an influenza A virus protective response which is subtype cross-protective. Influenza A virus NS1 protein, or a T cell epitope thereof, is administered to the individual in an amount sufficient to stimulate the virus protective response.

3 Claims, No Drawings

CROSS-REACTIVE INFLUENZA A IMMUNIZATION

RELATED APPLICATIONS

This application is a continuation of application Ser. No. 08/419,513 filed Apr. 7, 1995 which is is a file wrapper continuation of 08/042,884, filed Apr. 5, 1993 now abandoned, which is continuation-in-part of Ser. No. 07/564, 714, filed Aug. 8, 1990, now abandoned, the disclosure of which is incorporated herein by reference.

GOVERNMENT SUPPORT

The work described herein was funded by PHS Grants ROI-AI19378, ROI-A224750, and T32-AI07272.

BACKGROUND OF THE INVENTION

Influenza A virus is a large RNA-containing animal virus. The protein capsid of the virus is further enclosed in a lipid bilayer-based envelope containing protruding spikes of viral glycoprotein. Three influenza A serotypes have been identified (H1, H2 and H3); the classification based upon differences in the viral glycoprotein.

Upon infection by the Influenza A virus, the body produces antibodies to variable regions of the surface glycoproteins hemagglutinin (HA) and neuraminidase (NA). This response results in the production of virus-specific antibodies which constitute the primary defense of the immune system. These antibodies provide immunological pressure which leads to antigenic drift within viral subtypes, as well as shifts between viral subtypes. This relatively high rate of mutagenesis can render vaccine preparations ineffective because the antigenic determinants of the mutated viral proteins can differ significantly from those of the protein used as immunogen resulting in the failure of the body to effectively deal with the infection.

Two central components of the immune system are the B cells and T cells, both of which are lymphocytes. The lymphocyte lineage diverges at the prelymphoblast stage into distinct sublineages. B cells produce and secrete antibody molecules; a process generally referred to as the humoral response. T cells are responsible for a variety of cellular responses referred to generally as cell mediated immune responses.

B cells develop antigen specificity even in the absence of antigen stimulation. It has been estimated, for example, that the preimmune repertoire of a mouse comprises a class having many millions of different antibody molecules. This preimmune repertoire is apparently large enough to insure B cell specificity for almost any potential antigenic determinant.

Current inactivated whole or subunit influenza vaccines provide B cell mediated (humoral) immunity in that they induce antibodies which are directed toward antigenic determinants of the surface glycoproteins of the virus. The first presentation of an influenza antigen to a B cell specific for the antigen (e.g., at the time of vaccination) results in the maturation of the B cell into a plasma cell which is highly specialized for antibody production. Upon a second encounter with the same antigen, a rapid and increased secondary response results. The foreign antigen is bound by the specific antibody followed by clearance of the bound antigen from the bloodstream.

However, in the case of influenza A, the production of virus-neutralizing antibodies provides immunological pressure which leads to antigenic drift within viral subtypes, as well as shifts between viral subtypes. Vaccines which are directed against antigenic sites do not elicit a broadly cross-reactive (i.e., protective against all influenza A virus subtypes) B cell response. Furthermore, the mutations which result from this immunological pressure can render current vaccines ineffective.

T cells comprise a class of cells which, although they do not produce circulating antibodies, do play a central role in the immune system. The T cell class includes helper T cells, cytotoxic T cells and suppressor T cells. Helper T cells function, in part, by augmenting the response of other lymphocytes, for example, helper T cells stimulate activated T lymphocytes, in addition to stimulating B cells activation, by secreting interleukins as well as other soluble factors. Cytotoxic T cells (also referred to as killer T cells), on the other hand, function by destroying cells marked with a particular antigen (e.g., cells infected by virus).

T cells are stimulated by the recognition of a T cell epitope, in combination with a class I or a class II major histocompatibility (MHC) antigen, on the surface of an antigen presenting cell. Macrophages belong to the class of antigen presenting cells. Macrophages are phagocytes which ingest foreign particles in the body. These cells are capable of ingesting even large microorganisms such as protozoa. Following ingestion, the antigen presenting cell digests the foreign particle and fragments of the foreign particle are displayed on the surface of the cell.

T cell epitopes differ fundamentally from B cell epitopes. B cell epitopes are antigenic determinants found in the native antigen molecule and not represented in the denatured antigen or fragments thereof. T cell epitopes, on the other hand, are found on unfolded molecules or fragments thereof. Furthermore, the T cell epitopes comprise helper T cell epitopes and cytotoxic T cells epitopes. These epitopes are thought to be contained by distinct, albeit possibly overlapping, portions of the antigen molecule.

Influenza A virus infection continues to cause epidemics of death and tremendous morbidity throughout the world today even though the etiological agent is known. A great deal of effort has been devoted to the development of a vaccine, to little avail. A need exists for an effective influenza A vaccination strategy which could provide cross-subtype immunity from Influenza A viral infection.

SUMMARY OF THE INVENTION

This invention relates to Applicants' finding that T cell epitopes of the influenza A NS1 protein are capable of stimulating an influenza A virus protective response, in an individual, which is subtype cross-protective. In a first aspect, the method comprises administering an effective amount of influenza A virus NS1 protein, in combination with a pharmaceutically acceptable carrier thereby stimulating a T cell response against an NS1 epitope in the individual resulting in an influenza A virus protective response which is subtype cross-protective. A homologue of the NS1 protein in which amino acids have been deleted, inserted or substituted without essentially detracting from the immunological properties thereof, is also effective for this purpose.

In another aspect, the invention relates to a method and composition for immunizing an individual against infection by influenza A virus subtypes by the administration of an effective amount of an influenza A virus T cell epitope in combination with a pharmaceutically acceptable carrier, thereby stimulating a T cell response against the NS1 epitope in the individual resulting in an influenza A protective response which is subtype cross-protective. The T cell epitope can stimulate a cytotoxic T cell response, a helper T cell response, or both. A homologue of the NS1 T cell epitope in which amino acids have been deleted, inserted or substituted without essentially detracting from the immunological properties thereof, is also effective for this purpose.

The invention also relates to an essentially pure oligopeptide having an amino acid sequence corresponding to a T cell epitope of the influenza A NS1 protein. This T cell epitope can stimulate a cytotoxic T cell response, and/or a helper T cell response. Again, a homologue of the NS1 T cell epitope in which amino acids have been deleted, inserted or substituted without essentially detracting from the immunological properties thereof, is also effective for this purpose.

Also disclosed is a method for immunizing an individual against infection by influenza A virus subtypes comprising administering an effective amount of a recombinant virus which expresses the influenza A virus NS1 protein. The individual can also be immunized by administering an effective amount of a recombinant virus which expresses an influenza A virus T cell epitope. These methods are limited to the administration of a recombinant virus which expresses the NS1 protein or a T cell epitope thereof, thereby stimulating a T cell response against a T cell epitope resulting in an influenza A virus protective response which subtype cross-protective.

The methods and compositions described herein provide for a broadly cross-reactive vaccination scheme which is protective against H1, H2 and H3 subtypes of influenza A virus.

DETAILED DESCRIPTION OF THE INVENTION

As discussed previously, influenza A virus comprises three subtypes, H1, H2 and H3. Applicants' invention relates to methods for immunizing an individual, particularly a human, against infection by any of these subtypes. Although the methods described herein are particularly useful for human immunization, the methods are equally applicable to other mammals. The term "cross-protective" is used in this application to describe immunity against H1, H2 and H3 subtypes.

The gene encoding the influenza A NS1 protein has been isolated, cloned, and expressed in a recombinant vaccinia system (see e.g., *Bennink* et al., *J. Virol.* 61:1098–1102 (1987)). Using standard biochemical techniques (e.g., column chromatography) the NS1 protein, having a known molecular weight, can be isolated from cells in which it is expressed. If necessary to attain the desired purity, a hybridoma producing monoclonal antibody specific for NS1 can be generated. Monoclonal antibody produced by this hybridoma can then be used in an affinity capture purification scheme.

Homologues of the NS1 protein in which amino acids have been deleted, inserted or substituted without essentially detracting from the immunological properties thereof can be generated in a variety of ways. For example, in vitro mutagenic techniques can be used to modify the cloned gene encoding the NS1 protein. Such methods, which are well known to one skilled in the art, can be used to delete, insert or substitute nucleotides in the gene resulting in the deletion, insertion or substitution of amino acids in the encoded product. The immunological properties of the mutagenized encoded product can be assayed using methods such as those described in the Exemplification which follows.

Effective dosages for the stimulation of an influenza A virus protective response are determined empirically with initial dosage ranges based upon historical data for peptide/protein vaccine compositions. As used herein, the term virus protective refers to an immunological response in the individual resulting in the successful control or limitation of infection by influenza A virus subtypes which is clinically observed.

For example, individuals can be administered dosages of NS1 protein ranging from 0.5–500 micrograms. Whether a particular dosage is effective can be determined using well known T cell proliferation and cytotoxicity assays. For example, following administration of the protein to an individual blood is drawn. Cytotoxic T cells are identifiable by $^{51}Cr$ release assay (see e.g., Kuwano et al., *J. Virol.* 140:1264–1268 (1988)). Helper T cells are identifiable by a standard T cell proliferation assay (see e.g., Kurane et al., *J. Clin. Invest.* 83:506–513 (1989)). The results from these studies are compared with results from the same experiments conducted with T cells from the same individual prior to administration of the antigen. By comparing this data, effective dosage ranges can be determined.

A wide variety of pharmaceutically acceptable carriers are useful. Pharmaceutically acceptable carriers include, for example, water, physiological saline, ethanol polyols (e.g., glycerol or administration is typically parenteral (i.e., intravenous, intramuscular, intraperitoneal or subcutaneous). An adjuvant (e.g., alum) can also be included in the vaccine mixture.

The invention also pertains to a method for immunizing an individual against infection by influenza A virus subtypes by administering a vaccine composition comprising at least one essentially pure T cell epitope of the NS1 protein in combination with a pharmaceutically acceptable carrier. Due to genetic variability between individuals, a single T cell epitope may not stimulate a virus protective response in all individuals to whom it is administered. Therefore, by combining two or more distinct T cell epitopes, the vaccine is more broadly effective. As indicated above, helper T cell epitopes and cytotoxic T cell epitopes are thought to comprise distinct (albeit possibly overlapping) regions of proteins. Cytotoxic T cell epitopes can be distinguished from helper T cells epitopes experimentally using the cytoxicity and proliferation assays described above (helper T cells stimulate proliferation but do not posses cytotoxic activity).

The T cell epitope will be administered as an oligopeptide. Such oligopeptides can be synthesized chemically following identification of the portion of the protein containing the T cell epitope. Alternatively, a truncated portion of the gene encoding the NS1 protein which contains a T cell epitope can be expressed in a cell, and the. encoded product can be isolated using know methods (e.g., column chromatography, gel electrophoresis, etc.). In addition, the intact NS1 protein can be treated chemically or enzymatically to generate fragments which contain a T cell epitope. Such fragments can be isolated as described above.

As used herein, the term oligopeptide means any amino acid sequence which is identical or substantially homologous to a portion of the NS1 protein. The expression substantially homologous refers to oligopeptides having an amino acid sequence of an NS1 T cell epitope in which amino acids have been deleted, inserted or substituted without essentially detracting from the immunological properties thereof. This definition includes amino acid sequences of sufficient length to be classified as polypeptides (these terms are not used consistently or with great precision in the literature).

In a preferred embodiment, both a helper T cell epitope and a cytotoxic T cell epitope are administered to the individual. The stimulation of cytotoxic T cells is desirable in that these cells will kill cells infected by influenza A virus. The stimulation of helper T cells is beneficial in that they secrete soluble factors which have a stimulatory effect on other T cells, as well as B cells. As discussed above, due to the genetic variability between individuals, it is preferable to include two or more cytotoxic T cell epitopes and two or more helper T cell epitopes.

Several methods are described in the literature which are useful for the identification of T cell epitopes. For example, DeLisi et al. have suggested that potential epitopic sites may be located by identification of potential amphipathic alpha helical regions in the molecule. DeLisi et al., *Proc. Natl. Acad. Sci. USA* 82:7048 (1987). Bixler et al. describe a strategy of synthesizing overlapping synthetic peptides encompassing an entire protein molecule for delineation of T cell epitopes. Bixler et al., *Immunol. Com.* 12:593 (1983); Bixler et al. *J. Immunogenet.* 11:339 (1994). A synthetic method described by Gysen (*Ciba Foundation Symposium* 119:130 (1986)) permits synthesis of a large variety of peptides thereby mimicking of a variety of potential binding sites, in turn allowing rapid scanning of a molecule.

More traditional methods, such as enzymatic or chemical digestion of proteins provide peptide fragments which may be readily tested for T cell activity. For example, enzymes such as chymotrypsin, elastase, ficin, papain, pepsin, or trypsin provide limited and predictable fragments by cleavage of specified amino acid linkages; similarly chemical compounds such as N-chloro-succinimide BPNS-skatole, cyanogen bromide, formic acid, or hydroxylamine, also produce definable fragments by their action on proteins. The presence of the desired T cell stimulating activity in any given fragment can be readily determined by subjecting purified fragments to a standard T cell proliferation assay, or by analyzing unpurified fragments with a T cell Western Assay. Young et al., *Immunol.* 59:167 (1986).

In another embodiment, the gene encoding the NS1 protein, or a portion thereof which contains a T cell epitope, can be cloned into a recombinant virus which expresses the NS1 protein, or T cell epitope containing portion thereof, in the individual to be immunized. An example of such a recombinant virus system is the vaccinia system described by Paoletti et al. (U.S. Pat. No. 4,603,112), the disclosure of which is incorporated herein by reference. Other viruses have been described in the literature which have a genome which can accommodate the insertion of a foreign DNA such that a protein encoded by the DNA is expressed in vivo. Any such recombinant virus is useful for the practice of this invention.

One skilled in the art will recognize that the compositions described herein can be combined with the components of influenza A vaccines currently in use, thereby resulting in an improved vaccine. The invention is illustrated further by the following Exemplification.

EXEMPLIFICATION

Example 1

Adoptive Transfer In Mice

Mice

BALB/c mice (H-$2^d$) were purchased from Charles River Breeding Laboratories (Stone Ridge, N.Y.). They were used at 5 to 9 weeks of age.

Influenza Viruses

Influenza A viruses, A/PR/8 (H1N1), A/BZ (H1N1), A/JAP (H2N2), and A/PC (H3N2), or B/HK, were propagated in 10-day-old embryonated chicken eggs. Infected allantoic fluids were harvested 2 days after infection, aliquoted, and stored at −80° (Kuwano, K. et al., *J. Immunol.* 140:1264–1268 (1988)).

Vaccinia Viruses

Vaccinia recombinant viruses containing genes (HA, NP, NS1, and PB2) for A/PR/8 virus were kindly provided by Dr. B. Moss (Bethesda, MD). They were constructed and propagated as previously described (Smith, G.L. et al., *Virology* 160:336–345 (1987)). Briefly, HeLa cells were infected with virus for 3 days at 37°. Infected cells were pelleted by centrifugation, and resuspended in MEM containing 2% FCS. Three cycles of freezing and thawing were performed and the suspensions were gently sonicated in water for 1 min followed by trypsinization for 30 min at 37°. After centrifugation at 500 rpm for 5 min, supernatants were aliquoted and stored at −80°.

Cells

The cell lines used in this study, P815 cells (H-$2^d$; mastocytoma) derived from DBA/2 mice, Class 1 MHC molecules, H-2$L^d$- or H-2$D^d$-transfected L929 cell line, and LM1 ($K^k$, $L^d$, $D^k$) or DM1 ($K^k$, $L^k$, $D^d$), were as described by Weis, J. H. and J. G. Seidman (*J. Immunol.* 134:1999–2003 (1985)).

Fusion Protein

D proteins were produced in E. coli as described previously (Yamada, A. et al., *Escherichia coli. J. Exp. Med.* 162:663–674 (1985); Kuwano, K. et al., *J. Immunol.* 140:1264–1268 (1988)). Briefly, plasmids containing DNA fragments complementary to the viral RNA of A/PR/8 virus were manipulated to achieve expression of D proteins, which are hybrids of the first 81 amino acids of NS1 fused to the 157 amino acids from the C-terminal end of HA2 through a linker of glutamine-isoleucine-proline. After lysis of the bacteria, two 0.1% deoxycholate extractions and one 1% Triton X-100 extraction were performed to remove contaminating *E. coli* proteins, and the D protein was solubilized with 4 M urea at 4° for 30 min. The urea was removed by dialysis at 4°. The proteins were stored in 50 mM Tris-HC1, pH 8.0, and 1 mM EDTA. D protein was provided by J. F. Young (Smith, Kline and French Laboratories, Philadelphia, Pa).

CTL Clone

CTL clones were established as described previously (Kuwano, K. et al., *J. Immunol.* 140:1264–1268 (1988)). Briefly, CTL responder cells were stimulated weekly with A/PR/8 or D protein-pulsed normal syngeneic $^{\gamma}$-irradiated spleen cells in the presence of 10% Con A stimulated rat IL2 for several weeks. A limiting dilution was carried out to isolate CTL clones. The B-7 clone was established by stimulation of D protein (Kuwano, K. et al., *J. Immunol.* 140:1264–1268 (1988)). The A-11 clone was stimulated by A/PR/8 virus and grew, at a frequency of growth 2 out of 96 wells, from a well where two responder cells had been seeded. For routine passage of clones, $2\times10^6$ of clone cell were stimulated weekly by $30\times10^6$ of A/PR/8 virus or D protein treated $^{\gamma}$-irradiated spleen cells in the presence of 10% rat IL2 and $5\times10^{-5}$ M 2-ME.

CTL Assay

P815, LM1, or DM1 cells ($2\times10^6$) were incubated with 0.5 ml of virus ($10^7$–$10^8$ PFU) in the presence of $^{51}$Cr at 37° for 60 min. After three washings, target cells were incubated for another 1 hr. Then $1\times10^4$ $^{51}$Cr-labeled target cells were incubated with $1\times10^4$ effector cells in a total volume of 200 µl in 96-well round bottom microplates for 4 hr at 37°. The supernatant fluids were harvested and specific lysis was determined as percentage specific lysis=100× [(release by CTL−spontaneous release)/(maximum release−spontaneous release)].

Adoptive Transfer of CTL Clone Cells of the CTL clone ($3 \times 10^6$) were suspended in 0.5 ml of RPMI 1640 and injected into mice via the tail vein. A preliminary experiment indicated that transfer of $1.0 \times 10^6$ cells resulted in significant reductions in mean pulmonary virus titers (0.6–0.8 $\log_{10}$PFU) in recipients of clone A-11. Six hours after adoptive transfer of the CTL clone, mice were infected intranasally with $10^3$PFU of virus under ether anesthesia. The lungs of four mice per group were harvested 3 days later for measurement of virus titers.

Pulmonary Virus Titrations

Virus titrations were performed by plaque formation using MDCK cells as previously described (Kuwano, K. et al., *J. Immunol.* 140:1264–1268 (1988)). Briefly, infected lungs taken from recipient mice were manually homogenized in 1.5 ml of PBS containing 0.1% BSA. After centrifugation, the lung supernatants were serially 10-fold diluted in PBS. Diluted virus samples (100 μl ) were added to confluent MDCK cells in 24-well tissue culture plates and incubated at 37° for 1 hr. Each well then received 1 ml of 1% agar prepared as described earlier (Kuwano, K. et al., *J. Immunol.* 140:1264–1268 (1988)). After 2 days of incubation, 1 ml of 10% neutral red (GIBCO, Chagrin Falls, Ohio) in PBS was overlaid on the agar in the wells. Plaques were counted 8 hr later. The results were expressed as the mean $\log_{10}$ PFU/ml of duplicate samples.

Cross-Reactivity of Clone A-11 Stimulated by A/PR/8 Virus

Four CTL clones were established that were derived from A/PR/8 virus-immune spleen cells of BALB/c mice ($H-2^d$) stimulated by A/PR/8 virus (H1N1). Two of the CTL clones demonstrated H1 subtype-specific lysis of virus-infected target cells. These CTL clones were PB2 protein specific as determined using target cells infected with a vaccinia recombinant virus containing the gene for PB2 of A/PR/8 virus. Clone 1E8, representative of two subtype H1-specific clones, is shown as a negative control in Table 2. Clone A-11, which is representative of the other two CTL clones, demonstrated cross-reactive lysis of target cells which were infected with A/PR/8 (H1N1), A/BZ (H1N1), A/JAP (H2N2), or A/PC (H3N2) viruses, but failed to lyse B/HK-infected target cells (Table 1). The B-7 CTL clone (Kuwano, K. et al., *J. Immunol.* 140:1264–1268 (1988)) was used as a control. B-7 had been stimulated by a fusion protein containing part of the HA2 subunit of A/PR/8 virus and showed subtype H1H2 cross-reactive lysis of target cells that had been infected with A/PR/8 (H1), A/BZ (H1), or A/JAP (H2) viruses. The phenotypes of the cell surface antigens of both the A-11 and B-7 clones were Thy1+, Lyt-2+, and L3T4.

TABLE 1

Virus Specificity of Clone A-11 Stimulated by A/PR/8 Virus

| | | % Specific Lysis of P815 Target Cells | | | | | |
|---|---|---|---|---|---|---|---|
| Clone | E/T Ratio | A/PR/8 (H1N1) | A/BZ (H1N1) | A/JAP (H2N2) | A/PC (H3N2) | B/HK | Uninfected |
| A-11[a] | 1.0 | 54 | 59 | 58 | 62 | 0 | 0 |
| | 0.5 | 43 | 51 | 43 | 43 | 0 | 0 |
| B-7[b] | 1.0 | 62 | 65 | 43 | 0 | 1 | 0 |
| | 0.5 | 45 | 52 | 32 | 0 | 0 | 0 |

[a]Clone A-11 expresses 94% of Thy1.2, 86% of Lyt-2, and 5% of L3T4 surface Ag.
[b]Clone Bp7 expresses 97% of Thy1.2, 95% of Lyt-2, and 0% of L3T4 surface Ag.

CTL Clone A-11 is NS1-Protein Specific

To examine the influenza protein recognized by clone A-11, target cells were infected with recombinant vaccinia viruses containing various influenza genes of A/PR/8 virus and were used in CTL assays. As shown in Table 2, clone A-11 significantly lysed NS1-VAC-infected and A/PR/8 virus-infected P815 target cells as positive control. However, clone A-11 failed to recognize HA-VAC, NP-VAC, PB2-VAC, or parental VAC-infected P815 target cells. Clone B-7 as a negative control lysed HA-VAC-infected target cells as well as A/PR/8 virus-infected target cells, but did not lyse NP-VAC-or VAC-infected target cells. Clone 1E8, also derived from A/PR/8 virus-immune spleen cells by repeated stimulation with A/PR/8 virus as described above, recognized PB2-VAC-infected target cells or A/PR/8 virus-infected target cells, but failed to recognize NS1-VAC or HA-VAC-infected target cells; it is also included as a control. These results indicated that CTL clone A-11 recognizes the NS1 protein on influenza A virus-infected cells.

TABLE 2

Recognition of NS1 Protein of A/PR/8 Virus by Clone A-11

| | | % Specific Lysis of P815 Target Cells | | | | | |
|---|---|---|---|---|---|---|---|
| Clone | E/T Ratio | A/PR/8 | HA-VAC | NP-VAC | NS1-VAC | PB2-VAC | VAC | Uninfected |
| Experiment 1 | | | | | | | | |
| A-11 | 1.0 | 55 | −4 | ND | 42 | −4 | ND | −1 |
| | 0.5 | 47 | −4 | ND | 33 | −2 | | −2 |
| 1E8 | 1.0 | 61 | −3 | ND | 0 | 62 | ND | −1 |
| | 0.5 | 53 | −4 | ND | 0 | 47 | ND | −1 |
| Experiment 2 | | | | | | | | |
| A-11 | 3.0 | 78 | 0 | −1 | ND | ND | 0 | 1 |
| | 1.0 | 75 | 1 | −1 | ND | ND | 0 | 1 |
| B-7 | 3.0 | 91 | 91 | −1 | ND | ND | −2 | 0 |
| | 1.0 | 72 | 80 | −1 | ND | ND | −1 | 0 |

Reduction of Pulmonary Virus Titers by Transfer of NS1-Specific CTL Clone

To examine whether adoptive transfer of NS1 protein-specific CTL clone A-11 would reduce virus titers in the lungs of mice infected with influenza viruses, $3 \times 10^6$ cells of clone A-11 were adoptively transferred to BALB/c mice 6 hr prior to influenza infection. Three days later, lungs were removed for titration of influenza viruses. Virus titrations were performed by plaque formation assays in MDCK cells. Similar results were obtained in two experiments with mean decreases in pulmonary virus titers of about 1.0 $\log_{10}$. As shown in Table 3, adoptive transfer of CTL clone A-11 significantly reduced the virus titers in the lungs of mice infected with A/PR/8, A/JAP, or A/PC viruses, but did not reduce the virus titer in the lungs of mice infected with B/HK virus. These results reflect the in vitro cross-reactivity of CTL clone A-11 shown in Table 1.

TABLE 3

Reduction of Pulmonary Virus Titers by Adoptive Transfers of Clone A-11

| | | RECIPIENTS | |
|---|---|---|---|
| CTL | Virus | Virus Titer in Lungs[b] | |
| Clone A-11[a] | Challenge | Experiment 1 | Experiment 2 |
| + | A/PR/8 (N1N1) | 5.1 ± 0.4[c] | 5.7 ± 0.2[f] |
| − | A/PR/8 | 6.2 ± 0.3 | 6.8 ± 0.2 |
| + | A/JAP (H2N2) | 3.0 ± 0.6[d] | 3.3 ± 0.2[g] |

TABLE 3-continued

Reduction of Pulmonary Virus Titers by Adoptive Transfers of Clone A-11

| CTL | Virus | RECIPIENTS Virus Titer in Lungs[b] | |
|---|---|---|---|
| Clone A-11[a] | Challenge | Experiment 1 | Experiment 2 |
| − | A/JAP | 4.3 ± 0.2 | 4.4 ± 0.2 |
| + | A/PC (H3N2) | 4.0 ± 0.4[e] | 4.5 ± 0.4[h] |
| − | A/PC | 5.0 ± 0.1 | 5.7 ± 0.2 |
| + | B/HK | 4.1 ± 0.1 | ND |
| − | B/HK | 4.2 ± 0.1 | |

[a]Cells (3 × 10[6]) were transferred 6 hr before virus challenge; +, transferred; −, no cells transferred.
[b]Lungs were taken and virus titers were examined by plaque assays in MDCK cells 3 days after virus challenge.
[c]$P < 0.01$, Student's t test.
[d]$P < 0.02$, Student's t test.
[e]$P < 0.005$, Student's t test.
[f]$P < 0.005$, Student's t test.
[g]$P < 0.0005$, Student's t test.
[h]$P < 0.005$, Student's t test.

MHC Restriction of Target Cell Lysis by Clone A-11

L929 cells (H-2$^k$) transfected with genes encoding H-2D$^d$ (DM1 cells) and H-2L$^d$ (LM1 cells) were used to examine the MHC restriction of target cells lysis by CTL clone A-11. As shown in Table 4, CTL clone A-11 significantly lysed A/PR/8 virus-infected LM1 (H-2L$^d$) target cells, but failed to lyse A/PR/8 virus-infected DM1 (H-2$^d$) or A/PR/8 virus-infected DAP (H-2$^k$) target cells.

As a control, CTL derived from bulk cultures of A/PR/8 virus-immune BALB/c (H-2d) spleen cells that had been stimulated by A/PR/8 virus in the presence of IL2 for several weeks were also used in this experiment. These virus-stimulated CTL lysed LM1 or DM1 target cells infected with A/PR/8 virus, but did not kill A/PR/8 virus-infected DAP target cells. It was also observed that the CTL clone A-11 was unable to recognize A/PR/8 virus-infected peritoneal exudate cells of C3H.OL mice (H-2K$^d$, D$^k$). These results indicate that recognition by the CTL clone A-11 of NS1 on A/PR/8 virus-infected target cells is restricted by the H-2L$^d$ allele.

response in H-2$^d$ mice. The ability of an NS1 specific CTL clone to passively protect mice after adoptive transfer of the NS1 specific CTL clone was reported. There were significant decreases in lung virus titers of mice challenged with influenza A viruses of all three subtypes i.e., H1, H2 and H3. The influenza A NS1 gene was the kind gift of Dr. Robert Lamb of Northwestern University and the gene was truncated and expressed in vaccinia virus. The results shown in Table 5 indicate that a CTL epitope recognized by an influenza A NS1 cross-reactive CTL clone was located between amino acids 1–40 of NS1.

TABLE 5

Recognition of Epitope(s) on Influenza A Non-Structural Protein by Virus-Stimulated CTL from BALB/c Virus-Immune Spleen Cells in Bulk Culture
Percent specific lysis at E:T

| Target Cells Infected With: | 20.0 | 100 | 50 |
|---|---|---|---|
| A/PR/8 | 71.9 | 56.9 | 47.2 |
| VAC-entire NS1 | 74.1 | 40.3 | 14.9 |
| VAC2 (aa1-167) | 41.0 | 25.2 | 12.3 |
| VAC10 (aa1-40) | 43.5 | 19.4 | 16.2 |
| Vaccinia alone | −1.6 | 5.0 | 4.3 |
| Uninfected | 13.7 | 6.5 | 4.9 |

The results in Table 5 demonstrate that as a positive control virus-stimulated immune spleen cells killed virus-infected target cells and did not significantly kill uninfected target cells; moreover, the results demonstrate that target cells infected with recombinant vaccinia viruses expressing various regions of the NS1 gene including the VAC-10 recombinant with amino acids 1–40 were significantly killed by the influenza virus stimulated PBMC. These results indicate that following a single infection with influenza A virus, significant memory CTL activity to epitopes on influenza A NS1 is present in H-2$^d$ mice.

Active Immunization with VAC/NS1 Recombinant Virus

It was important to determine if it was possible to actively immunize mice with a recombinant virus containing an NS1 gene segment to protect against influenza virus. An NS1-specific cross-reactive CD8+CTL responses had been detected in bulk cultures and at the clonal level, and protection in passive immunization studies with an NS1-

TABLE 4

MHC Restriction of CTL Recognition by CTL Clone A-11

| | | % Specific Lysis of Target Cells | | | | | |
|---|---|---|---|---|---|---|---|
| | | LM1 (H-2K$^k$, D$^k$, L$^d$) | | DM1 (H-2K$^k$, D$^k$, D$^d$) | | DAP (H-2K$^k$, D$^k$) | |
| CTL | E/T Ratio | A/PR/8 | None | A/PR/B | None | A/PR/8 | None |
| A-11 | 5.0 | 58 | 1 | 9 | 2 | 0 | 0 |
|  | 2.5 | 43 | 1 | 2 | 2 | 2 | 0 |
| A/PR/8 | 5.0 | 36 | 2 | 24 | 2 | 1 | 1 |
| stimulated CTL | 2.5 | 30 | 1 | 11 | 1 | 1 | 1 |

Example 2
Active Immunization In Mice
Active Immunization with the Recombinant Vaccinia Virus Expressing NS1 CTL Epitope is Protective in Mice In Example 1, results were presented that demonstrated an influenza A NS1 cross-reactive cytotoxic T lymphocyte specific clone had been shown, but active immunization with a vaccine had not been carried out.

Mice were immunized with 0.2 ml (1×10[8] PFU/ml) of a control vaccinia virus or the recombinant vaccinia-10 which contained the gene segment encoding influenza A NS1 amino acids 1–40. A second dose of 0.2 ml with the same amount of virus was administered IP to the two groups of mice three weeks later. Five weeks after the initial dose and two weeks following the second dose spleen cells were removed restimulated in vitro with A/PR/8 and then used in a CTL assay.

The results in Table 6 indicate that influenza A virus-specific CTL memory was induced following administration with the vaccinia-10 recombinant and boosting in vitro with influenza A virus. These cells killed influenza A virus infected target cells, and uninfected target cells were not lysed. The spleen cells of the control mice that were primed with vaccinia virus not containing the NS1 gene, were restimulated with live influence virus but their cells did not specifically lyse influenza A virus infected target cells. These results indicate that the priming of influenza A virus NS1 specific T cells resulted in the subsequent generation of influenza A virus cytotoxic T lymphocytes following repeat stimulation with influenza A virus.

TABLE 6

Vaccinia Virus Containing Gene Encoding NS1 aa1-40 Induces Influenza Virus CTL Memory in BALB/c (H-2$^d$) Mice Lysis of H-2$^d$ Target Cells

| 1° In Vivo | 2° In Vitro | E:T | A/PR/8 infected | Uninfected |
|---|---|---|---|---|
| VAC-10 (NS1-segment) | A/PR/8 | 30 | 11.2 | −1.3 |
|  |  | 10 | −1.0 | 4.4 |
| Vaccinia | A/PR/8 | 30 | −1.0 | 1.6 |
|  |  | 10 | 1.8 | 5.6 |

Seven weeks after the original immunization, mice in these groups were challenged with 4×10$^3$ plaque forming units of virulent influenza A/PR/34 (H1N1) virus administered in 50 μl volumes intranasally. The results from these experiments demonstrated that mice immunized with VAC/1 were significantly protected against lethal challenge with influenza A virus compared to mice given vaccinia virus alone (P<0.05). More specifically, the survival rate of VAC/NS1 immunized mice observed at 9–16 days post-infection was between 70–80%. The survival rate of mice infected with vaccinia virus alone (negative control) was about 20% during the same time period. It was important to determine if active immunization would induce protection against disease and death because Stitz et al. reported that a recombinant vaccinia virus which expressed the nucleoprotein (NP) gene of influenza A virus contained a CTL epitope did not protect when a recombinant vaccinia virus containing the gene for influenza nucleoprotein was used to immunize mice, even though a CTL clone specific for NP epitope was protective in passive transfer experiments.

The nucleoprotein gene induced influenza A virus memory CTL's in vaccinated mice but did not induce protection against subsequent infection(s). The results presented herein demonstrate that mice which had received the vaccinia expressing a segment of the influenza A NS1 gene had CTL memory responses and were protected against lethal challenge. In conclusion, these results demonstrate that influenza A NS1 virus contains protective CTL epitope (s) and can be used as a vaccine to protect against influenza mortality in mice. The results below indicate that humans also have influenza A NS1-specific CTL's.

Example 3

Generation & Characterization of a Human Influenza NS1-Specific T Cell Line

Method of Establishing Human NS1-Specific T Cell Line #77

Human PBMC were stimulated in bulk culture by exposure to influenza A/PR/8/34 (H1N1) infected autologous stimulator cells (1.6×10$^6$) which had been infected with virus at a multiplicity of infection of 10 to 1 for ninety minutes. After two washes these cells were added to 7×10$^6$ responder PBMC in AIM V medium containing 15% human AB serum. Following six days of culture, the cells were tested for their ability to lyse autologous EBV-transformed B cells in a standard 51 chromium release assay. Table 7 demonstrates results at two effector: target ratios, 50 and 10:1. There is specific lysis of the autologous target cells infected with influenza virus.

TABLE 7

| Effector cells | Percent Specific Lysis of Target Cells at E:T Ratio | | | |
|---|---|---|---|---|
|  | Uninfected | | A/PR/8 Infected | |
| A/PR/8 Stimulated | 50 | 10 | 50 | 10 |
|  | 10.7 | 7.9 | 45.6 | 33.9 |

On day 8, cells from the original culture were re-stimulated with x-irradiated autologous PBMC which had been infected with influenza A virus, similar to the methods used on day 0. On day 14, a limiting-dilution was performed and 60 wells each received either 10 cells, or 30 cells per well in AIM V media, with 10% fetal calf serum 10% T cell growth factor 0.1 microgram per ml of anti-CD3 mab and x-irradiated autologous PBMC cells. Fifteen days later, positive growth was seen in 27 of the 60 wells that were seeded at 10 cells per well, and 52 wells of the 60 that were seeded at 30 cells per well. Three wells were positive in cytotoxicity experiments and the cells in well #77 lysed influenza virus infected autologous BLCL but has very little lytic activity on the human NK sensitive cell K562 (13.1% vs. 2.1%). The next day, the cells in well #77 were fed and expanded by being re-stimulated every 14 days with the addition of x-irradiated PBMC and anti-CD3 antibody in the presence of AIM V medium and 10% fetal bovine serum and 10% T cell growth factor. The results in Table 8 show the killing activity of cells from well #77 on autologous BLCL target cell infected with the vaccinia/1 recombinant virus that contained the NS1 gene of influenza A virus infected with influenza A virus A/PR/8/34, but they did not kill target cells infected with vaccinia virus along or vaccinia viruses expressing the influenza A virus hemagglutinin gene, the nucleo protein gene. The results indicate that cells from well #77 specifically killed autologous target cells that expressed the influenza A NS1 gene.

TABLE 8

Lysis of Autologous B-LCL Target Cells Infected with Recombinant Vac/Influenza Viruses by Clone/Line #77

| Effector Cells #77 | E:T | A/PR/8 | VAC | VAC HA | VAC NP | VAC NS1 | Uninfected |
|---|---|---|---|---|---|---|---|
|  | 10 | 55:0 | −4.9 | −7.9 | −11.4 | 32.1 | −19.5 |

Three weeks later, the T cell line #77 was tested on target cells infected with an influenza A (A/PC/1/73, H3 subtype)

virus. These target cells were also killed to a high degree, as were target cells infected with the vaccinia recombinant virus expressing the NS1 truncated gene, but #77 cells did not kill target cells infected with recombinant vaccinia viruses expressing the other genes, hemagglutinin or nucleoprotein, of the influenza A virus. These results demonstrate that clone/line #77 specifically kills autologous cells expressing epitope(s) localized within amino acids 1–167 of the influenza A NS1 protein.

TABLE 9

Specific-Lysis by Clone #77 of Autolosous B-LCL Infected with Vaccinia, Expressing Truncated Influenza A Virus NS1 Gene Segments
Percent specific-lysis of target cells

| Effector Cells #77 | ET | VAC-entire NS1 1-237aa | VAC-NS1 (aa1-167) | VAC-NS1 (aa1-81) | Influenza A/PC/73 (H3N2) |
|---|---|---|---|---|---|
|  | 10 | 71.4 | 67.1 | 34.4 | 75.2 |

HLA Restriction of Influenza A NS1 Specific Cytotoxic T Lymphocyte Activity

Experiments were performed using allogeneic target cells which contained partially matched HLA alleles to define the HLA restriction allele used by the NS1 specific T cell line #77. The results of the first experiment shown in Table 10 demonstrate that allogeneic target cells that share HLA A1 and B8 alleles were killed and that target cells that shared B44 or CW5 were not killed. In the second experiment partially matched B-LCL target cells from three different donors were used, two of which shared only A1 and one of which shared only the B8 allele. The results demonstrate that allogenic target cells bearing the HLA B8 allele are killed, but those that shared only A1 were not. In summary, these results clearly demonstrate the existence of a human Class I restricted, influenza A virus NS1 subtype cross-reactive cytotoxic T lymphocyte responses.

TABLE 10

HLA Class I Restriction of #77, NS1-Specific Human CTL Percent Specific Lysis of HLA Partially Matched Cells

| HLA Shared | | | VAC-/NS1 (entire) |
|---|---|---|---|
| A. Autologous | | | |
| (A1 | B8 | B44 CW5) | 69.7 |
| A1 | B8 | | 64.0 |
| | | B44 CW5 | −7.1 |
| A1 | B8 | | 73.3 |
| B. Autologous | | | 78.5 |
| A1 | | | −2.1 |
| | B8 | | 59.6 |
| A1 | | | −0.7 |

Equivalents

Those skilled in the art will know, or be able to ascertain using no more than routine experimentation, many equivalents to the specific embodiments of the invention described herein. These and other equivalents are intended to be encompassed by the following claims.

What is claimed is:

1. A method for immunizing an individual against disease caused by infection by influenza A virus comprising administering to the individual an effective amount of an influenza A virus NS1 protein or an influenza A virus NS1 protein derivative in which amino acids have been deleted, inserted or substituted without essentially detracting from the immunological properties thereof, in a carrier such that said NS1 protein or NS1 protein derivative stimulates a protective NS1-specific cytotoxic T cell response.

2. The method of claim 1 wherein the NS1 protein derivative consists essentially of an NS1 T cell epitope.

3. The method of claim 1 wherein the NS1 protein is administered.

* * * * *